United States Patent [19]
Hofmann

[11] Patent Number: 5,462,520
[45] Date of Patent: Oct. 31, 1995

[54] TRANSSURFACE DRUG DELIVERY BY ELECTROFUSION OF MICROBUBBLES TO THE TISSUE SURFACE

[75] Inventor: Gunter A. Hofmann, San Diego, Calif.

[73] Assignee: Genetronics, Inc., San Diego, Calif.

[21] Appl. No.: 219,970

[22] Filed: Mar. 30, 1994

Related U.S. Application Data

[63] Continuation-in-part of Ser. No. 931,061, Aug. 17, 1992, Pat. No. 5,318,514.

[51] Int. Cl.⁶ .............................. A61N 1/30; A61K 38/00
[52] U.S. Cl. ..................... 604/20; 428/402.2; 424/449
[58] Field of Search ........................ 604/19, 20; 607/149, 607/150, 153; 428/402.2; 424/448, 449, 450

[56] References Cited

U.S. PATENT DOCUMENTS

| | | | |
|---|---|---|---|
| 4,921,757 | 5/1990 | Wheatley et al. | 428/402.2 |
| 4,955,378 | 9/1990 | Grasso et al. | 128/421 |
| 5,002,527 | 3/1991 | Reller et al. | 604/20 |
| 5,019,034 | 5/1991 | Weaver et al. | 604/20 |
| 5,098,843 | 3/1992 | Calvin | 435/287 |
| 5,137,817 | 8/1992 | Busta et al. | 435/173 |
| 5,149,539 | 9/1992 | Ledger et al. | 424/449 |
| 5,160,741 | 11/1992 | Cormier et al. | 424/449 |
| 5,162,043 | 11/1992 | Lew et al. | 604/20 |
| 5,236,413 | 8/1993 | Feiring | 604/21 |
| 5,312,325 | 5/1994 | Sibalis | 604/20 |

Primary Examiner—Lee S. Cohen
Assistant Examiner—Stephen Huang
Attorney, Agent, or Firm—Baker, Maxham, Jester & Meador

[57] ABSTRACT

A method of transtissue molecular delivery comprises encapsulating molecules to be delivered in a microbubble carrier, contacting a selected area of a tissue surface with a solution of the encapsulated molecules, and applying an electric field of sufficient amplitude to induce electrofusion between the tissue and the membrane of the microbubble.

18 Claims, 3 Drawing Sheets

TRANSSURFACE DRUG DELIVERY BY ELECTROFUSION OF MICROBUBBLES TO THE TISSUE SURFACE

REFERENCE TO RELATED APPLICATION

The present application is a continuation-in-part of application Ser. No. 07/931,061, entitled "APPLICATOR FOR THE ELECTROPORATION OF DRUGS AND GENES INTO SURFACE CELLS", Aug. 17, 1992 now U.S. Pat. No 5,318,514.

BACKGROUND OF THE INVENTION

The present invention relates to drug delivery and pertains particularly to a method and apparatus for the transtissue delivery of drugs and other molecules.

In my aforementioned application, I disclose an apparatus and method for the electroporation of drugs and genes into surface cells. In another co-pending application Ser. No. 07/907,322, entitled ELECTROPORATION METHOD AND APPARATUS FOR INSERTION OF DRUGS AND GENES INTO ENDOTHELIAL CELLS, filed Jul. 1, 1992, certain methods and apparatus are disclosed for insertion of drugs and genes into endothelial cells. It is often desirable to transport drugs and genes across or beyond a layer of surface tissue.

In the aforementioned parent application, I disclose methods and apparatus tier the electroporation of drugs and genes into surface cells. In that application, apparatus is disclosed for delivery of a fluid medium carrying preselected molecules to a skin surface and thereafter applying electrical signals by means of electrodes to the surface tissue. The field is applied at a predetermined strength and duration in order to make the walls of the cells of the skin transiently permeable to permit the macromolecules to enter the preselected cells without damaging them.

One difficulty with the prior apparatus is that the stratum corneum (SC) consists of a thin layer of dead cells with a high electrical resistance. This presents a major obstacle to the administration of drugs and genes transdermally. This layer can be perforated by the administration of short electrical field pulses, such as used in electroporation of cells. However, in the case of stratum corneum it appears more appropriate to speak in terms of dielectric break down of the stratum corneum.

Among the prior art relating generally to this field is the Weaver et al patent U.S. Pat. No. 5,019,034 entitled "Control of Transport of Molecules Across Tissue Using Electroporation". He describes a proposal for using high voltage, short duration electrical pulses on the tissue surface to produce electroporation of the tissue. However, he does not address or solve the problem of the obstacle provided by the stratum corneum, or how to drive the drugs into the tissue.

Another patent of interest is that of Grasso U.S. Pat. No. 4,955,378 entitled "Apparatus and Methods for Performing Electrofusion at Specific Anatomical Sites". He discloses a method of fusing biological particles to living tissue, preferably on corneas and in cervical areas. The tissue consists of living cells which are able to completely fuse with the biological particles, or live cells. Again, this does not address or solve the problem presented by the resistance of the stratum corneum. Also, neither of these patents provide or suggest any means to force the drugs or genes into or across the tissue surface.

The present invention was devised to overcome the problems of the prior art by providing means to overcome the resistance to the administration of drugs transdermally presented by the stratum corneum. It is also applicable to the transport of drugs and genes across surfaces of other tissue such as membranes.

SUMMARY AND OBJECTS OF THE INVENTION

It is the primary object of the present invention to provide an improved method of transdermal drug delivery by electrofusion.

In accordance with the primary aspect of the present invention, drugs or genes are loaded into microbubbles, the microbubbles are brought into physical contact with the tissue surface and a pulsed electrical field is applied between the microbubbles and the tissue by means of electrodes. This forms pores at the interface of the microbubbles and the tissue, such that the microbubbles fuse with the tissue and form a channel through which drugs and genes, which are under pressure, enter through the tissue.

BRIEF DESCRIPTION OF THE DRAWINGS

The above and other objects and advantages of the present invention will be appreciated from the following specification when read in conjunction with the accompanying drawings wherein.

DETAILED DESCRIPTION OF THE PREFERRED EMBODIMENTS

The present invention takes advantage of electrofusion of microbubbles to transfer drugs and genes across the surface tissue and possibly into the blood stream and, if desirable, subsequent electroporation to improve the uptake of drugs, genes, DNA or the like, into cells in the living tissue of humans and other living organism. Electrofusion is used to perform a fusion of drug-loaded vesicles to the skin. Electrical field pulses are then used to create dielectric breakdown of the tissue or the stratum corneum or other tissue surface forming passages through which the drugs and genes are transferred from the vesicles through the stratum corneum or surface tissue into the underlying tissue.

Electroporation involves the transient formation of pores in tissue or cell membranes utilizing a short pulse of high-voltage electric fields. Once these pores are formed in the cell membranes, DNA and other molecules can enter the cells through these pores in the cell walls. Thereafter, they stay encapsulated in the cell and the cell walls reseal themselves. The DNA or other gene or drug can then act within the cell to alter the cell properties.

Figure 1:
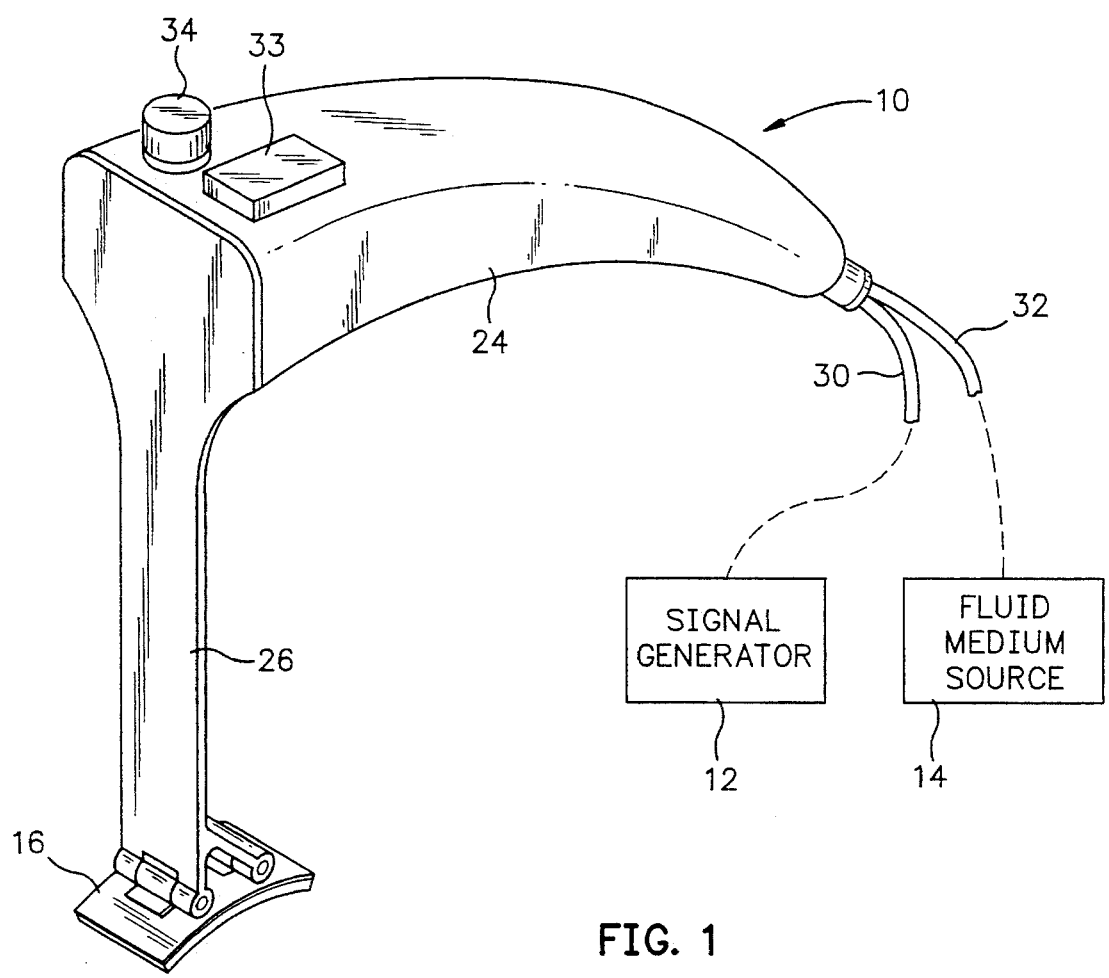
FIG. 1 is a perspective view of an apparatus for carrying out the process of the present invention.
Figure 2:
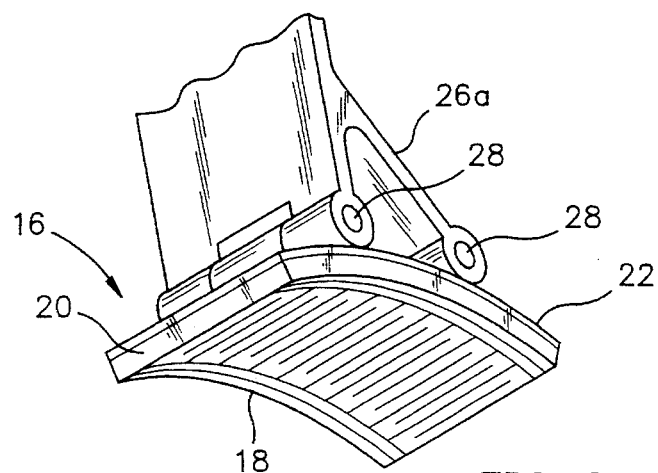
FIG. 2 is an enlarged view of the head assembly of the FIG. 1 embodiment.

Referring to FIG. 1, an exemplary embodiment of an apparatus which may be utilized in carrying out the process of the present invention, is illustrated. The device comprises a manually positionable applicator designated generally by the numeral 10 which is connected to a signal generator 12 and a fluid medium source 14. The applicator 10 has a head assembly 16 which engages and applies genes or drugs; and electrical pulses to a preselected surface tissue region of a patient. Details of the head assembly are illustrated in FIG. 2. The head assembly comprises an electrode array 18 which is carried or mounted on an open pore foam elastomer 20 carried by flexible semirigid or firm dielectric planar support member 22. Adjacent parallel segments of the conductors serve as electrodes for application of the electric field to the tissue surface.

The applicator 10 (FIG. 1) further includes a handle portion 24 and an arm portion 26 on which is mounted the head assembly 16. The head assembly 16 is connected to a Y-shaped distal end 26a by means of a pair of pins 28. These pins enable the head to flex and conform to the curvature of the skin surface.

The terminal ends of the conductor 18 are connected to the signal generator 12 by way of an electrical cable 30. A fluid medium carrying the molecules or drugs is contained within the fluid medium source 14, which may include a suitable motorized pump or pressure source, not shown. The fluid medium source 14 is coupled to the elastomer foam 20 by flexible tube 32 which extends to the applicator 10 to the foam applicator. An actuator button 30 on the handle 24 of the applicator may be depressed to activate a valve (not shown) and deliver a suitable quantity of the fluid medium to the foam elastomer 20. The elastomer 20 provides a sponge-like substrate for holding a predetermined quantity of the fluid medium. The applicator and signal generator functions as more fully described in the aforementioned parent application, now allowed, which is incorporated herein by reference as though it were fully set forth.

The invention can also be carried out by apparatus and methods disclosed in the aforementioned Ser. No. 07/907, 322 which is incorporated herein by reference as though fully set forth. This provides a more convenient apparatus for the delivery of drugs and genes across tissue surfaces and membranes such as in body cavities. The present invention was devised to overcome the problem presented by the stratum corneum. However, it is applicable to the insertion of molecules such as drugs and genes across other tissue surfaces in body cavities and open wounds. Certain modifications may be necessary to the illustrated apparatus for these other applications.

Figure 3:
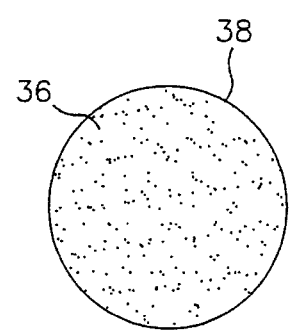
FIG. 3 is a diagrammatic illustration of a microbubble and a first-step of loading drugs or genes into microbubbles.

Referring to FIG. 3, the process of the present invention is carried out by first encapsulating the drugs or genes 36 which are to be delivered transdermally into microbubbles 38 as carriers. These microbubbles can be liposomes, erythrocyte ghosts or other vesicles. The encapsulation of the molecules can be carried out by any one of a number of known processes, including electroporation.

Figure 4:
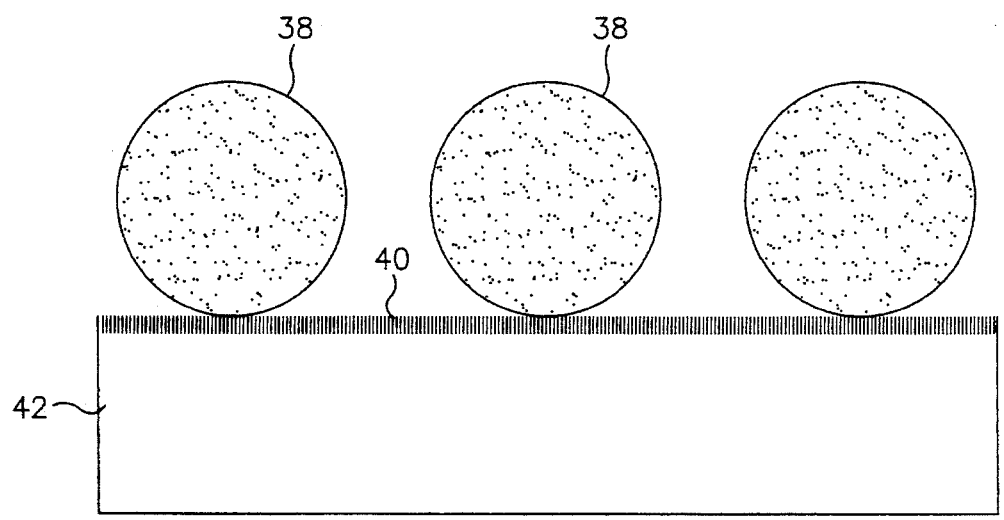
FIG. 4 is a diagrammatic illustration of multiple microbubbles applied to the skin.

The loaded microbubbles 38, as illustrated in FIG. 4, are then brought into contact with the tissue surface or stratum corneum 40 of a skin layer 42 by suitable means and are positioned between pairs of closely spaced electrodes 44 and 46. This can be carried out by the apparatus of FIG. 1, wherein a fluid carrying the microbubbles and applied by the sponge 20 would be positioned between the electrodes 18 on the surface of the applicator.

Figure 5:
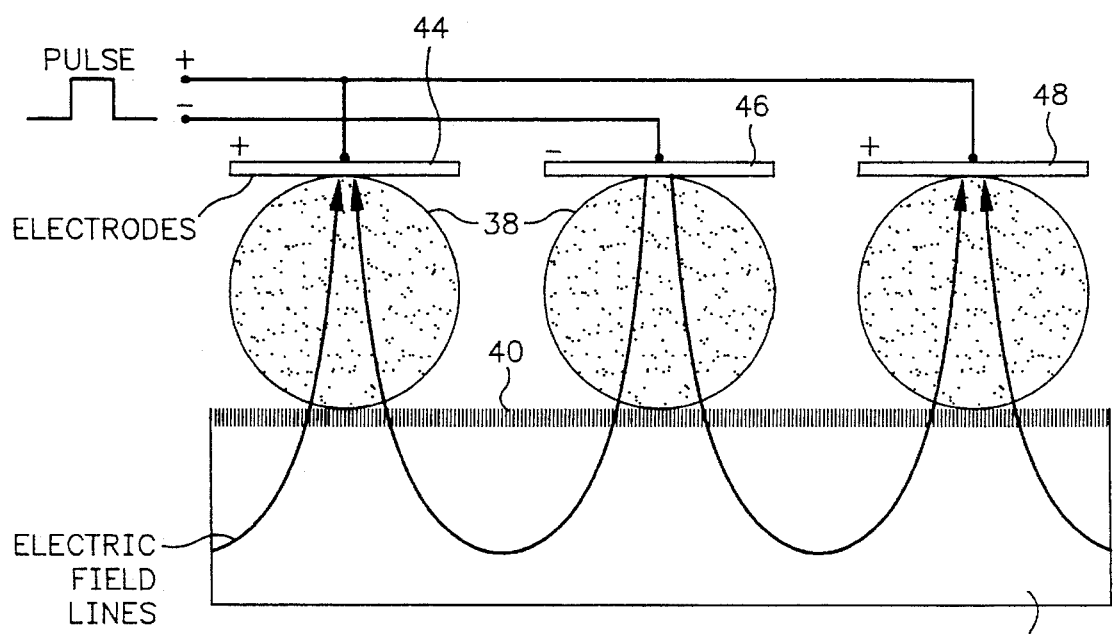
FIG. 5 is a diagrammatic illustration of a third step of applying a pulse electrical field between the microbubbles and skin.

Thereafter, a short voltage pulse is applied between the electrodes so that the electric fields of sufficient amplitude are generated to induce dielectric breakdown in the stratum corneum and the membrane of the microbubbles. As shown in FIG. 5, the electric field is applied so that useful electric field lines are perpendicular to the tissue surface or stratum corneum surface. Typical electrical parameters for the stratum corneum are a field strength of 0.5–5 kV/cm, with a pulse length of 10 usec to 10 msec. This electric field induces a dielectric breakdown in the stratum corneum and the microbubbles. Other tissue surfaces will typically require less field strength.

Figure 6:
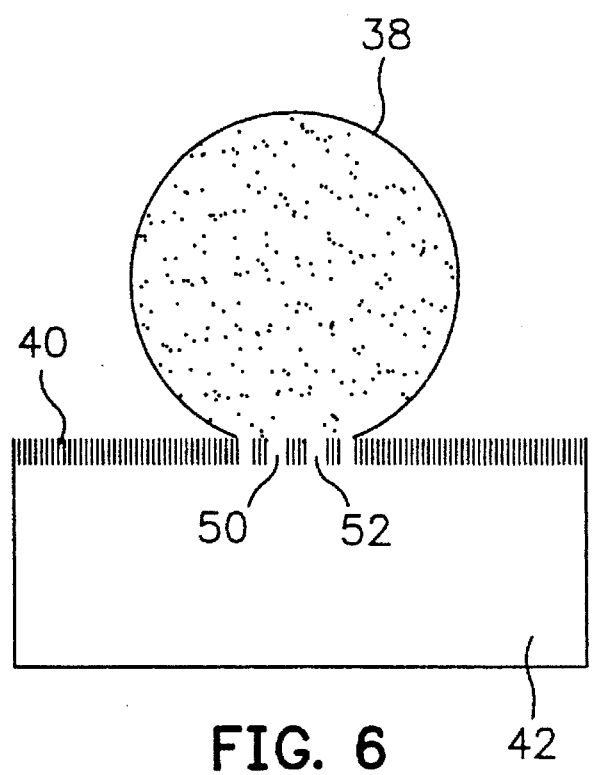
FIG. 6 is a diagrammatic illustration of the formation of pores at the interface of microbubbles and the stratum corneum.
Figure 7:
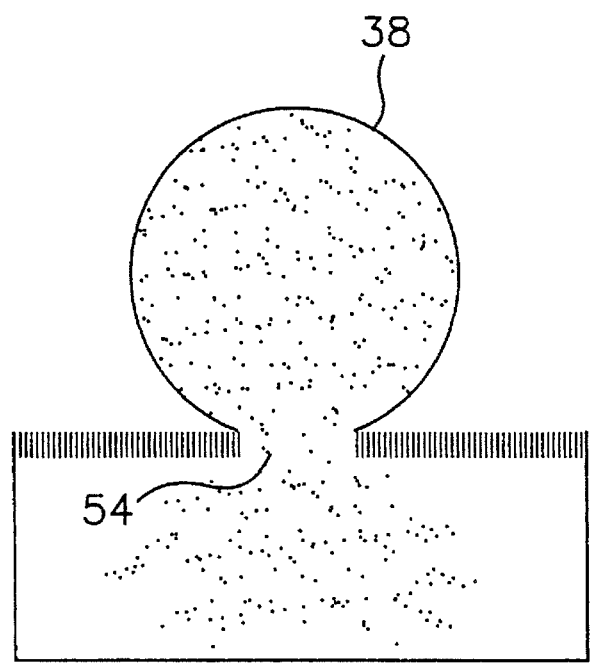
FIG. 7 is a diagrammatic illustration of the fusion of the microbubbles with the stratum corneum and the passage of drugs or genes through channels in the stratum corneum.

The dielectric breakdown in both the stratum corneum and the microbubbles generate or open pores 50 and 52 as illustrated in FIG. 6. These pores open up and can join into one lumen and create a channel 54 through which the contents of the microbubbles empty through and into the dermis underlying the stratum corneum as illustrated in FIG. 7. Pressure within the microbubbles can act to drive the fluid through the channel or channels. Since the stratum corneum consists essentially of dead material, the channel will not close as quickly as it would in a live tissue. This allows the drugs or genes to diffuse through the surface layer into the underlying skin tissue.

Other forms of a delivery system could be utilized, such as a small system strapped to the arm or other body part or momentarily connected, containing a rechargeable battery-powered pulse power supply with a reservoir containing microbubbles in suspension with the drug encapsulated. The applicator would have the basic components as the device in FIG. 1 such that by pushing one button, a preselected amount of microbubbles is delivered to the skin between the electrodes. The microbubbles are pressed against the skin for good mechanical contact. Activating another button or switch delivers an electrical pulse to the electrodes which fuse the microbubbles to the stratum corneum. A large number of the microbubbles are then fused to the skin and start pumping the drug through the stratum corneum.

A special patch can also be applied to the tissue surface. The microbubbles can be contained in the patch which also contains the electrode structure to create the electric field. The electrode structure can be similar to FIG. 2 and inside the patch. The electrode structure is connected to two electrodes outside the patch so that a pulse generator can be connected momentarily to these outside electrodes to provide a voltage pulse. The patch is preferably provided with an adhesive border to adhere it to the skin or tissue. It is also preferably provided with a protective cover which can be peeled off before adhering the patch to the skin or tissue.

If the drug is to be transported into the cells, a second pulse after allowing appropriate diffusion time, is applied to open up pores in the cells. This allows the cells to take up the drug or molecules as in electroporation.

A drug delivery time profile can be created by mixing different size microbubbles. The flux can then be controlled by the pore size and the number of microbubbles delivered. The process of the present invention could also be combined with iontophoresis as an additional driving force. The iontophoresis takes advantage of ion charges to cause a migration of the ions or molecules through existing passages or pores in the tissue. The combination could use electroporation to open up channels and pores and then use electrophoresis to induce migration of the drugs or genes further into selected tissue.

The present invention has been demonstrated in experiments as follows:

1. Labelled calcein was placed on the skin of a nude mouse.
2. Labelled calcein was placed on the mouse skin, then electroporated.
3. Labelled calcein was encapsulated in liposomes, then placed on the mouse skin.
4. Labelled calcein was encapsulated in liposomes, then placed on the mouse skin and electrofused to the skin.

The results of this limited experiment showed that the best penetration of the skin into the underlying skin or tissue was seen in Example 4, with the liposome-encapsulated calcein which had been electrofused to the skin.

I have illustrated and described my invention by means of specific embodiments, it is to be understood that numerous changes and modifications may be made therein without departing from the spirit and scope of the invention as defined in the appended claims.

I claim:

1. A method of trans surface tissue molecular delivery comprising the steps of:

selecting a quantity of microbubble carriers, selecting a quantity of molecules to be delivered across the surface tissue;

encapsulating said molecules within said microbubble carriers;

contacting a selected area of the surface tissue with a quantity of said carriers containing said encapsulated molecules; and applying a pulsed electric field of sufficient amplitude and duration to induce electrofusion between the surface tissue and said microbubbles and create pores in the surface tissue to enable diffusion of the molecules from said microbubble carriers through the surface tissue.

2. A method according to claim 1 wherein said electric field has a strength of from 0.5–5 kV/cm with a pulse length of from 10 usec to 10 msec.

3. A method according to claim 1 wherein the microbubbles are liposomes.

4. A method according to claim 3 wherein said electric field has a strength of from 0.5–5 kV/cm with a pulse length of from 10 usec to 10 msec.

5. A method according to claim 1 wherein the microbubbles are liposomes carried in a liquid.

6. A method according to claim 5 wherein said electric field has a strength of from 0.5–5 kv/cm with a pulse length of from 10 usec to 10 msec.

7. A method according to claim 1 wherein the tissue surface contacted is a stratum corneum.

8. A method according to claim 7 wherein the microbubbles are liposomes carried in a liquid.

9. A method according to claim 8 wherein said electric field has a strength of from 0.5–5 kv/cm with a pulse length of from 10 usec to 10 msec.

10. A method of delivering molecules across surface tissue, comprising the steps of:

selecting a quantity of molecules to be delivered across the tissue;

selecting a quantity of microbubbles as carriers for said molecules;

encapsulating said molecules to be delivered into said microbubbles;

contacting a selected area of the surface tissue with a quantity of said microbubbles containing said encapsulated molecules; and applying an pulsed electric field of sufficient amplitude and duration to induce electrofusion between the tissue and said microbubbles and create passages in the tissue for the dispersion of said molecules from said microbubbles through said surface tissue.

11. A method according to claim 10 wherein said electric field has a strength of from 0.5–5 kV/cm with a pulse length of from 10 usec to 10 msec and field lines extending normal to the tissue surface.

12. A method according to claim 11 wherein the microbubbles are liposomes suspended in a liquid.

13. A method according to claim 10 wherein the tissue surface is a stratum corneum.

14. A method according to claim 13 wherein the microbubbles are liposomes carried in a liquid.

15. A method according to claim 10 wherein the tissue surface is a tissue surface in an open wound.

16. A method according to claim 15 wherein the microbubbles are liposomes carried in a liquid.

17. A method according to claim 10 wherein the tissue surface is a membrane in a body cavity.

18. A method according to claim 17 wherein the microbubbles are liposomes carried in a liquid.

* * * * *